United States Patent

Neward

Patent Number: 5,163,944
Date of Patent: Nov. 17, 1992

[54] OBSTETRICAL VACUUM EXTRACTOR

[76] Inventor: Theodore C. Neward, P.O. Box 725, Cucamonga, Calif. 91730

[21] Appl. No.: 742,920

[22] Filed: Aug. 9, 1991

[51] Int. Cl.⁵ .............................................. A61B 17/42
[52] U.S. Cl. ...................................... 606/123; 604/74
[58] Field of Search ....................... 606/123, 122, 124; 604/74

[56] References Cited

U.S. PATENT DOCUMENTS

| | | | |
|---|---|---|---|
| 667,447 | 2/1901 | Miller | 604/74 X |
| 897,289 | 9/1908 | Howell | 604/74 |
| 2,542,505 | 2/1951 | Gasciogne | 604/74 |
| 3,202,152 | 8/1965 | Wood et al. | 606/123 |
| 4,730,617 | 3/1988 | King | 606/123 |
| 4,799,922 | 1/1989 | Beer et al. | 604/74 |
| 5,019,086 | 5/1991 | Neward | 606/123 |

FOREIGN PATENT DOCUMENTS 617016  3/1961  Canada .............................. 606/123

*Primary Examiner*—Peter A. Aschenbrenner
*Attorney, Agent, or Firm*—Lyon & Lyon

[57] ABSTRACT

There is disclosed herein a vacuum extractor for use in childbirth and comprising a bell shaped cup having a relatively thin outer flared edge, a hollow stem extending from the cup, and the stem including a handle. A vacuum source can be connected to the stem to draw a vacuum within the cup. A liner is hooked over the flared edge of the cup and provides a relatively large soft and resilient bead for the outer edge of the vacuum extractor which contacts maternal and fetal tissue. The liner is stretched into and secured within the cup and includes an aperture for allowing a vacuum to be drawn within the cup.

7 Claims, 2 Drawing Sheets

OBSTETRICAL VACUUM EXTRACTOR

BACKGROUND OF THE INVENTION

The field of the present invention relates to an apparatus for facilitating the extraction of a child during childbirth.

In some instances during childbirth, a completely natural birth is not possible an assistance must be rendered by the attending physician in order for the child to be delivered. Such assistance may be rendered with forceps or other similar devices, but these devices tend to be bulky and difficult to operate, and their use introduces some chance of injury or discomfort to the mother and child. An alternative to forceps is a vacuum extractor device which uses a vacuum cup for attachment onto the head of the child. Joined to the cup is an elongated stem which is used to manipulate the cup. The physician may then apply a pulling force, accompanied by proper positioning, to be transmitted to the child's head by manipulation of the stem of the device.

An existing obstetrical vacuum extractor is disclosed in U.S. Pat. No. 3,202,152. That patent describes a vacuum operated device, more specifically a vacuum cup, for attaching to the head of a child, and an elongated stem joined to the cup which is used to manipulate the cup thereby enabling a pulling force to be applied to the child's head. A similar vacuum extractor is manufactured and sold by Neward Enterprises, Incorporated of Cucamonga, Calif.

Although the foregoing forms of vacuum extractors have met with considerable success, the Neward vacuum cup has a relatively flexible edge which is used in contact with the head of the baby, and the flexibility facilitates forming a good seal. However, because of the need to provide a relatively thin edge so as to maintain the desired flexibility, the edge of the cup in some instances possibly could abrade or injure the maternal or fetal tissue.

SUMMARY OF THE INVENTION

Accordingly, the present invention is an improvement over such prior vacuum extractors and eliminates the foregoing problem by providing a soft, flexible coating to give maximum comfort to the patient during application and use but without hindering the superior flexibility and maneuverability of the above noted prior form of vacuum extractor.

In an exemplary embodiment, the conventional Neward Enterprises vacuum extractor is provided with a soft pliable liner or membrane so as to minimize trauma to maternal tissue, as well as enable every portion of the fetal scalp that is exposed to the vacuum action of the vacuum cup of the vacuum extractor to be cushioned by the liner or membrane so as to virtually eliminate trauma to the surfaces being contacted or adhered to by the vacuum action of the cup.

Accordingly, it is a principal object of the present invention to provide an improved form of obstetrical vacuum extractor.

Another object of this invention is to provide a vacuum extractor for childbirth comprising a substantially conventional extractor and vacuum cup but having a soft liner over the edge of the cup which comes in contact with the maternal tissue and fetal scalp.

BRIEF DESCRIPTION OF THE DRAWINGS

These and other objects and advantages of the present invention will become better understood through a consideration of the following description taken in conjunction with the drawings in which.

DETAILED DESCRIPTION OF THE PREFERRED EMBODIMENT

Figure 1:
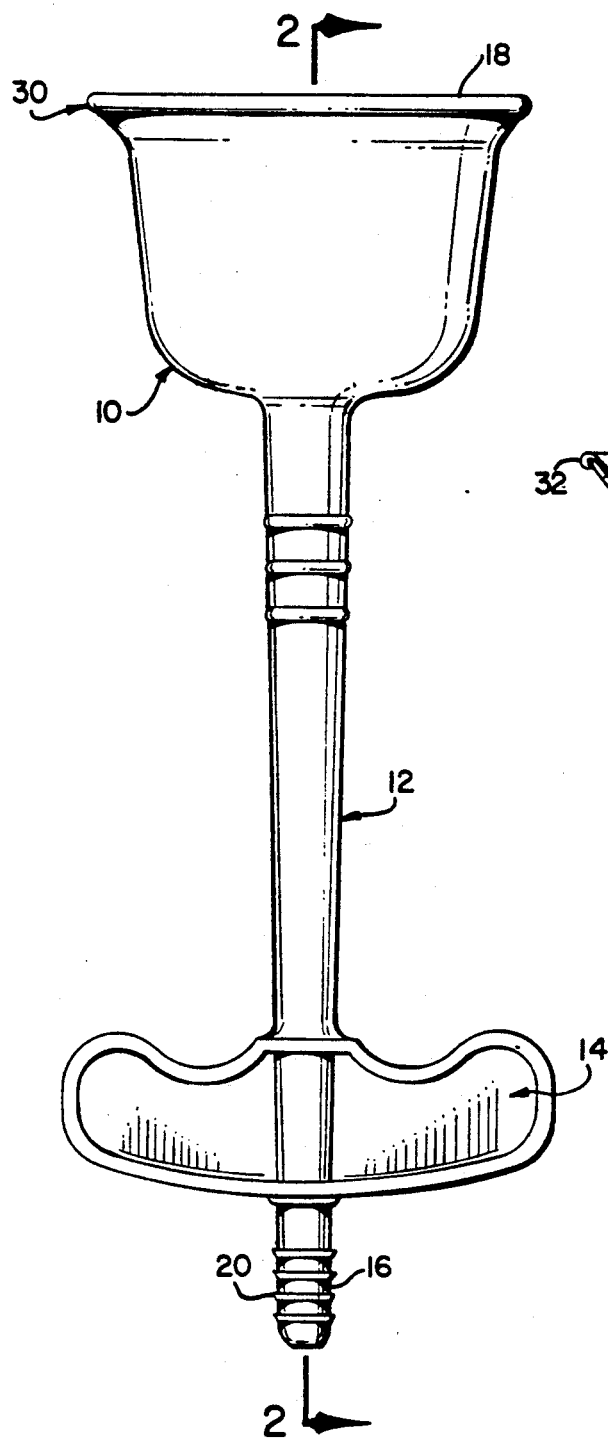
FIG. 1 is a side view of a conventional vacuum extractor of the type previously noted as manufactured by Neward Enterprises, and having thereon a liner in accordance with the present invention.
Figure 2:
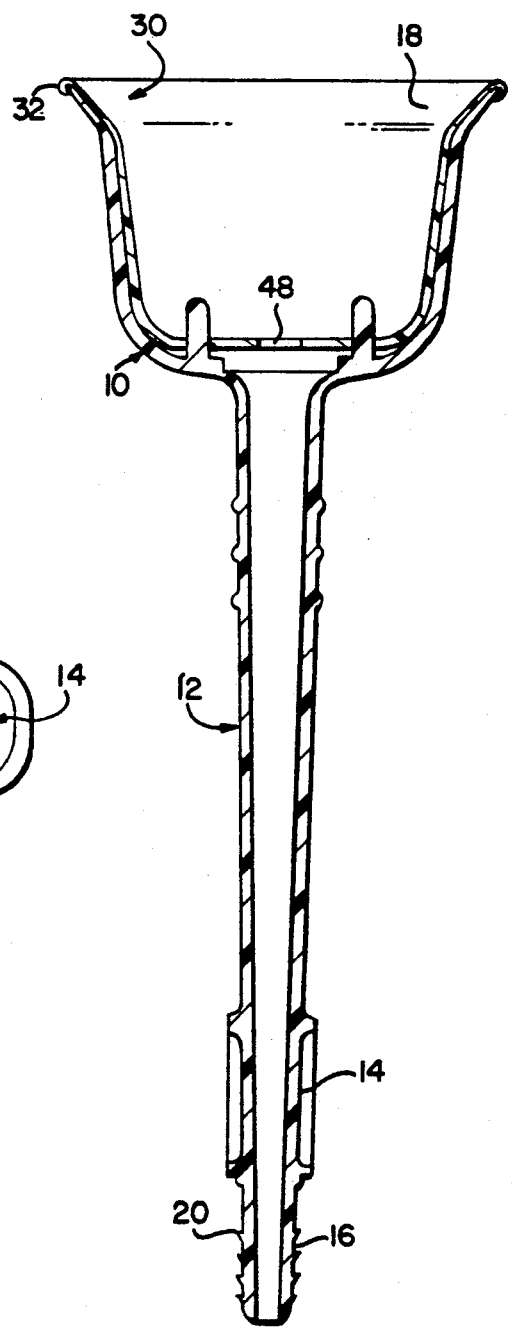
FIG. 2 is a cross-sectional view of the extractor, taken along line 2—2 of FIG. 1, further illustrating in detail the liner.

The present invention provides an improvement over the extractor device disclosed in U.S. Pat. No. 3,202,152, the disclosure of which is incorporated herein by reference. It also is an improvement over the vacuum extractor sold by Neward Enterprises as noted earlier and which is sold under the trademark MITY-VAC. FIGS. 1 and 2 illustrate the existing Neward Enterprises vacuum extractor, but the same also further incorporates the present invention.

The vacuum extractor of FIG. 1 comprises a vacuum cup 10, an elongated hollow stem 12 and a handle 14. The distal end 16 of the stem 12 is opened to the hollow inside and is designed to couple with a suitable plastic tube which, in turn, is connected to a suitable vacuum source (not shown). Operation of the vacuum source draws air through an open end 18 of the cup 10, through the hollow interior of the stem 12 and through the distal end 16. Ribs 20 at the distal end 16 of the stem 12 insure an airtight connection with the vacuum hose. The handle 14 facilitates manipulation of the overall extractor, particularly when manipulating and pulling the child from the mother.

Figure 3:
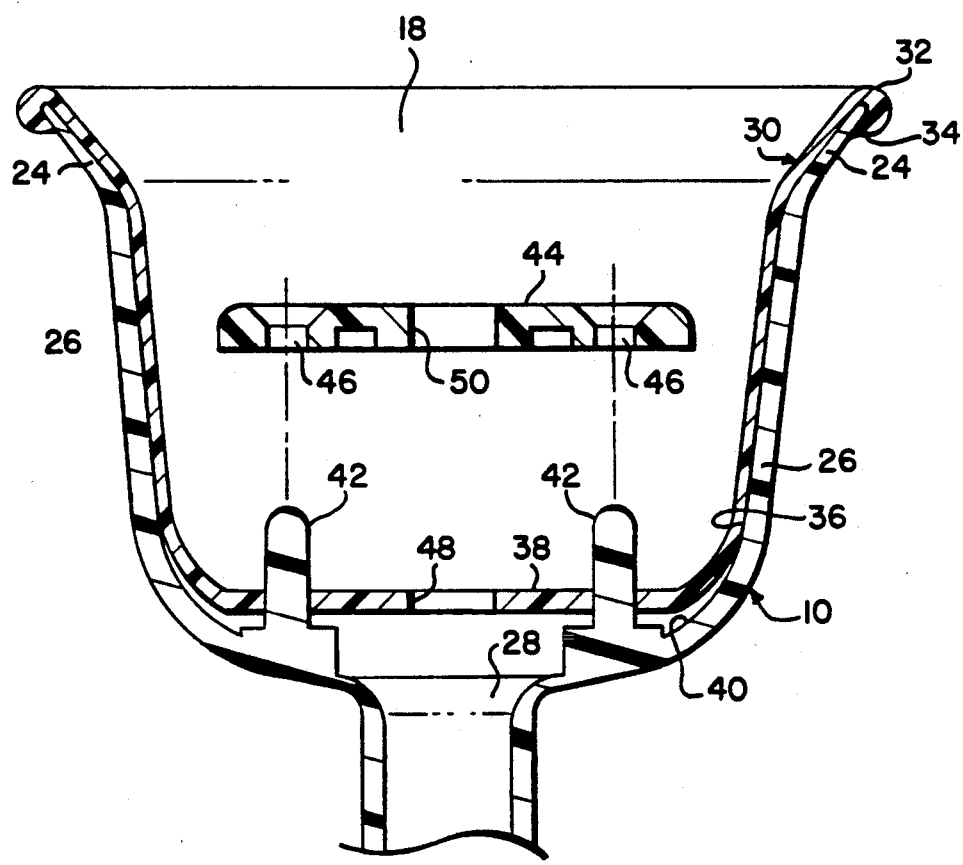
FIG. 3 is an enlarged cross sectional view of the vacuum cup (taken along lines 2—2 of FIG. 1) and means for attaching the liner to the vacuum cup.

The vacuum cup 10 preferably has a bell shape as shown in FIGS. 1-3, and has a thinner and flexible outer edge 24. An exemplary diameter of the outer edge 24 is 2.375 inch and depth of the cup is 1.70 inches. A typical range of thickness of the primary distal portion 26 of the cup 10 preferably is approximately 0.065–0.068 inch; whereas, the thin edge 24 tapers down to a thickness of preferably about 0.028–0.032 inch. This flexible edge 24 has been provided in the past so as to be sufficiently flexible to facilitate providing a good seal with the skin of the head of the baby. The cup 10 has an opening 28 which communicates with the hollow interior of the stem 12 and thus with the open distal end 16 of the stem. The extraction thus far described is conventional.

It is desirable to have a cup with a soft flexible edge 24 so as to provide a good seal with the skin of the baby's head and to conform to irregularities and the baby hair if present. The present inventor tried providing a bead on the edge 24 of the cup but this caused a loss of the needed flexibility. The vacuum extractor needs to have a proper balance of edge flexibility, and body rigidity so as to maintain a good seal at the opening 18 of the cup 10 while at the same time providing some rigidity for enabling a certain degree of manipulation of the baby during delivery.

In accordance with a preferred embodiment of the present invention, a soft flexible coating or liner 30 is provided which overlies the thin edge 24 of the cup 10, and extends into and is secured within the inside of the cup 10 as particularly shown in FIG. 3. The liner 30 is of soft rubber or rubber-like material, such as Silastic rubber, and it is formed essentially in the shape of a bell, conforming to the interior shape of the cup 10. The liner has a relatively large bead 32 which wraps around and hooks over the cup edge 24 at 34. The hook action appears to be sufficient, but the liner could be welded or cemented at 34 to the rim 24.

The liner 30 then extends into the cup 10 and conforms to the inner surface 36 of portion 26 of the cup 10 and terminates in an inner planar bottom section 38. The liner 30 is molded of the rubber or rubber-like material to have the configuration seen in FIGS. 2-3 such that the planar bottom section 38 does not normally extend all the way to the inside base surface 40 of the cup 10 but, rather, the liner has to be stretched by applying a liner disk 44 which pushes the planar surface 38 toward the base 40 of the cup 10. The distance between the planar surface 38 and the base 40 can be approximately 0.05 inch.

The base 40 of the cup 10 includes a pair of pegs 42 like in the conventional Neward Enterprises extractor, and the disk 44 is in the shape of a circular disk and has a pair of apertures 46 through which the respective pegs 42 extend and can be sonic welded to the disk. Thus, by pushing the disk 44 down onto the pegs 42, and welding the pegs to the disk, the liner 30 is stretched to tightly conform to the inner surface 36 of the cup 10. A typical thickness for the major portion of the liner 30 is 0.030 inch, with the base section 38 having a typical thickness of 0.05 inch. The base 38 of the liner 30 has a suitable hole 48 aligned with hole 28, and the disk 44 has a similar hole 50 to allow the vacuum to communicate between the inside of the cup 10 and the hole through the stem 12.

Thus, the liner 30 is hooked over the flared edge 24 of the cup 10 and stretched down into the middle of the cup 10 and secured and held tightly by the rigid disk 44. The liner is maintained under tension so as to retain secure engagement through the large bead 34 over the edge 24 and to conform to the flared outer edge 24 and inner wall 36 of the cup 10. The relatively large bead 32 provides a soft and non-abrading contact area during insertion and manipulation of the vacuum extractor and attachment to the head of the baby.

While an embodiment of the present invention has been shown and described, various modifications may be made without departing from the scope of the present invention, and all such modifications and equivalents are intended to be covered.

What is claimed is:

1. An obstetrical vacuum extractor comprising
   a vacuum cup substantially in the shape of a bell having a relatively thin outer flared edge and a thicker body portion and a base section connected with a hollow stem,
   the stem having an open end for connection to a vacuum source,
   the stem including a handle for facilitating manipulation of the vacuum extractor, and
   a flexible liner having an outer bead engaged with and extending over the outer flared edge of the cup, and the liner extending into the cup and having a base section secured to the base section of the cup.

2. A vacuum extractor as in claim 1 wherein the liner is formed of a rubber or rubber like material having a wall thickness of approximately 0.03 inch and base section thickness of approximately 0.05 inch.

3. An obstetrical vacuum extractor comprising
   a vacuum cup substantially in the shape of a bell, the vacuum cup having a body section with a relatively thin outwardly flared edge at an open end of the cup an having a base section opposite the open end,
   an elongated stem extending from the base section of the cup, the stem being hollow with an opening therethrough communicating with the inside of the cup and a distal end of the stem for connection to a vacuum source, and
   the stem including a handle for facilitating manipulation of the vacuum extractor, and the cup, stem and handle being molded as a unitary unit from plastic, the improvement comprising
   a flexible liner disposed within the cup, the flexible liner having an outer bead extending over and hooked with the outer flared edge of the cup, the liner extending into the inside of the cup to the base section and being secured to the base section of the cup by a rigid disk secured to the base section of the cup.

4. A vacuum extractor as in claim 3 wherein the liner is formed of rubber or rubber like material, and the rigid disk is secured to pegs extending from the base section of the cup.

5. An obstetrical vacuum extractor comprising
   a vacuum cup substantially in the shape of a bell having a relatively thin outer flared edge and a thicker body portion and a base section connected with a hollow stem,
   the stem having an open end for connection to a vacuum source,
   the stem including a handle for facilitating manipulation of the vacuum extractor, and
   a flexible liner having an outer bead engaged with and extending over the outer flared edge of the cup, and the liner extending into the cup and having a base section secured to the base section of the cup, the liner being secured within the cup by a rigid circular disk secured to pegs extending from the base section of the cup.

6. An obstetrical vacuum extractor comprising
   a vacuum cup substantially in the shape of a bell having a relatively thin and flexible outer flared edge and a thicker body portion extending to a base section, the base section being connected with a hollow stem,
   the stem having an open end for connection to a vacuum source,
   the extractor including a handle for facilitating manipulation of the vacuum extractor, and
   a flexible liner on and within the cup, the liner having an outer bead covering engaged with and extending out over the outer flared edge of the cup, and the liner extending into the cup and being bonded to the base section of the cup.

7. The vacuum extractor as in claim 6 wherein the liner is bonded within the cup by a rigid circular disk secured to the base section of the cup.

* * * * *